(12) United States Patent
Zimnitsky et al.

(10) Patent No.: US 8,597,264 B2
(45) Date of Patent: Dec. 3, 2013

(54) APPARATUSES, METHODS, AND COMPOSITIONS FOR THE TREATMENT AND PROPHYLAXIS OF CHRONIC WOUNDS

(75) Inventors: Dmitry Zimnitsky, San Antonio, TX (US); Jenny Finkbiner, Helotes, TX (US)

(73) Assignee: KCI Licensing, Inc., San Antonio, TX (US)

( * ) Notice: Subject to any disclaimer, the term of this patent is extended or adjusted under 35 U.S.C. 154(b) by 292 days.

(21) Appl. No.: 13/071,387

(22) Filed: Mar. 24, 2011

(65) Prior Publication Data

US 2012/0245540 A1    Sep. 27, 2012

(51) Int. Cl.
*A61M 1/00* (2006.01)

(52) U.S. Cl.
USPC ......................................... 604/313

(58) Field of Classification Search
USPC .......... 604/304, 313, 319; 602/46, 48, 50, 56; 424/443, 447, 449, 473, 476, 485, 486, 424/492, 498, 502, 520
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

N. A. Bagautdinov, "Variant of External Vacuum Aspiration in the Treatment of Purulent Diseases of the Soft Tissues," *Current Problems in Modem Clinical Surgery: Interdepartmental Collection*, edited by V. Ye Volkov et al. (Chuvashia State University, Cheboksary, U.S.S.R. 1986); pp. 94-96 (certified translation).

(Continued)

*Primary Examiner* — Melanie Hand

(57) ABSTRACT

According to an illustrative embodiment a method to promote healing of a wound is provided comprising contacting the wound with a biologically active composition comprising a lipoic acid derivative and gelatin. In another embodiment a topical composition is provided, which can be formulated as a homogenous mixture, such as a spray, mist, aerosol, lotion, cream, solution, oil, gel, ointment, paste, emulsion or suspension or applied on a carrier material, such as a bandage, gauze, foam, sponge, hydrogel, hydrocolloid, hydrofiber, occlusive dressing, adhesive composition or scaffold. Methods for producing such a topical composition and carrier material with the topical composition applied thereto are also disclosed.

11 Claims, 4 Drawing Sheets

(56) References Cited

U.S. PATENT DOCUMENTS

| | | | |
|---|---|---|---|
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61(1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written 0pinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

(56) References Cited

OTHER PUBLICATIONS

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, p. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Ðukić, Ž. Maksimović, Ð. Radak, and P. Peška, "Vacuum Therapy in the Treatment of Peripheral Blood Vessels," *Timok Medical Journal* 11 (1986), pp. 161-164 (certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

Alpha Lipoic Acid 200 mg; http://www.seacoast.com/supplement/natural-factors-alpha-lipoic-acid-200-mg-60-caps-13; viewed Mar. 30, 2011.

APPARATUSES, METHODS, AND COMPOSITIONS FOR THE TREATMENT AND PROPHYLAXIS OF CHRONIC WOUNDS

BACKGROUND

The present invention relates generally to compositions and methods for medical treatment of wounds, and more particularly, medical dressings, systems, and methods employing alpha-lipoic acid and its pharmaceutically acceptable salts and derivatives, for treatment or prophylaxis of chronic wounds.

Typical procedures for treating chronic wounds such as, for example, venous ulcers, diabetic ulcers and pressure sores, include the use of absorbent dressings or hydrocolloid gels. Additionally, since most chronic wounds are infected, many wound dressings contain antimicrobial agents, such as silver or iodine, to either create a barrier to microorganisms or reduce microbial load. These treatments are used more for managing the wound environment and moisture balance than actively promoting wound healing.

Inflammation and the timely release of reactive oxygen species (ROS) are critical for normal wound repair and, together with proteolytic and other cytotoxic enzymes, serve to kill ingested bacteria and prevent wound infection. However, due to other circumstances such as patient nutrition, co-morbidities (smoking, diabetes), or poor blood circulation due to patient positioning, the inflammatory phase may last too long resulting in the creation of excess ROS that actually damage surrounding tissue including healthy tissue forming within the wound. Excess ROS, also known as "free radicals," can be detrimental to tissue because they also damage cells and extracellular matrix components such as collagen. Additionally, ROS can act as signaling molecules to recruit matrix metallo proteases (MMPs) and other proteases to the wound site. Normal endogenous levels of MMPs are essential for tissue remodeling during the wound healing process. However, in excess, they continually break down the new tissue that is formed. This leads to a wound that either does not heal quickly or becomes "stalled." Excess levels of ROS and MMPs create a sustained state of inflammation thereby preventing the progression of normal wound healing.

Elevated levels of MMPs have been remedied by preventing activation of MMPs or by use of MMP inhibitors. Some wound dressings on the market use various forms of natural collagen as a sacrificial substrate for MMPs because the collagen also provides the mechanical properties (integrity) necessary to form the dressing. Topical application of antioxidants to a wound may reduce ROS levels, subsequently helping a chronic wound to re-enter a normal healing state.

SUMMARY

According to an illustrative embodiment, a method for promoting healing of a wound is provided comprising contacting a wound site with a topical composition that is biologically active comprising a lipoic acid derivative and, optionally, a sacrificial proteolytic enzyme substrate, such as gelatin. Topical compositions, such as those provided, may be formulated as a homogenous mixture, for example as a spray, mist, aerosol, lotion, cream, solution, oil, gel, ointment, paste, emulsion or suspension. Methods for producing a homogenous mixture comprising a lipoic acid and a sacrificial proteolytic enzyme substrate are also provided. In certain aspects, a biologically active topical composition is applied to a carrier material, such as a bandage, gauze, foam, sponge, hydrogel, hydrocolloid, hydrofiber, occlusive dressing, adhesive composition or scaffold, which can be positioned at a wound site. Methods for production of a wound dressing with a biologically active composition applied thereto are also provided.

The present invention provides the use of alpha-lipoic acid and its pharmaceutically acceptable salts and derivatives, for the preparation of a composition for treatment or prophylaxis of chronic wounds. In certain aspects, a lipoic acid derivative is formulated with a sacrificial proteolytic enzyme substrate, such as gelatin, in a composition for treating a wound. In one embodiment a wound site is contacted with the composition to promote wound healing and reduce inflammation.

DETAILED DESCRIPTION

Figure 1A:
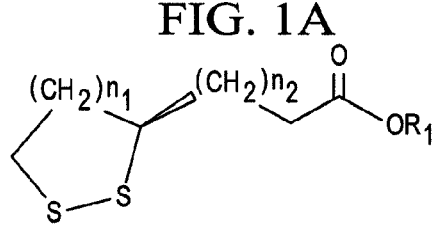
FIG. 1A is a chemical formula of certain derivatives of alpha-lipoic acid or pharmaceutically acceptable salts or derivatives thereof.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "homogenous mixture" refers here in to a uniformly blended mixture. In one embodiment, topical compositions of the present invention are prepared by thoroughly mixing or blending a lipoic acid derivative and proteolytic enzyme substrate to obtain a homogenous mixture. The composition may optionally be mixed with a pharmaceutically acceptable carrier and one or more optional ingredients or adjuvants. If necessary or desired, the resulting homogenous mixture can then be shaped or loaded into tablets, capsules, pills, canisters, cartridges, dispensers and the like or applied to a carrier material, such as a bandage, gauze or wound dressing using conventional procedures and equipment.

The term "pharmaceutically acceptable" as used herein refers to ingredients, agents or compositions within the term described are suitable for pharmaceutical administration without undue toxicity, incompatibility, instability, irritation, allergic response and the like. A "pharmaceutically acceptable salt" can be derived from pharmaceutically acceptable inorganic or organic bases and from pharmaceutically acceptable inorganic and organic acids, which are known in the art and can be derived by one of ordinary skill in the art.

The term "topical" application refers to application to the skin, dermis or wound site, and application to such wound sites includes application to the tissue site adjacent to or within the wound. Such wound sites encompass chronic, acute, traumatic, subacute, deep tissue and dehisced wounds, wounds from burns and ulcers, such as diabetic and pressure wounds.

The term "tissue site" as used herein includes, without limitation, a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location. The tissue may be that of any mammal, such as a mouse, rat, rabbit, cat, dog, pig, or primate, including humans, that are being treated as patients. Also, the wound at the tissue site may be due to a variety of causes, including trauma, surgery, degeneration, and other causes.

The term "biologically active composition" as used herein refers to a composition formulated with a lipoic acid derivative and, optionally, a gelatin. Such compositions may be formulated in any pharmaceutically acceptable carrier and will typically comprise an amount of lipoic acid derivative effective to reduce reactive oxygen species and inflammation at a tissue site. Gelatin for use according to the invention may be from any tissue source, such as from bovine, equine, or porcine tissues. Formulations and components for biologically active compositions are further detailed below. A "topical composition" as used herein refers to a composition designed for topical application or application to the skin or a wound.

As discussed above, normal endogenous levels of MMPs are essential for tissue remodeling during the wound healing process. However, in excess, they continually break down the new tissue that is formed. This leads to a wound that either does not heal quickly or becomes "stalled." Excess levels of ROS and MMPs create a sustained state of inflammation thereby preventing the progression of normal wound healing. Accordingly, in certain aspects, the invention provides methods for promoting wound healing by providing a biologically active topical composition comprising a lipoic acid derivative and a proteolytic enzyme substrate in an amount effective to reduce the level of ROS and MMPs and/or reduce inflammation at the wound site and in surrounding tissue.

Figure 1B:
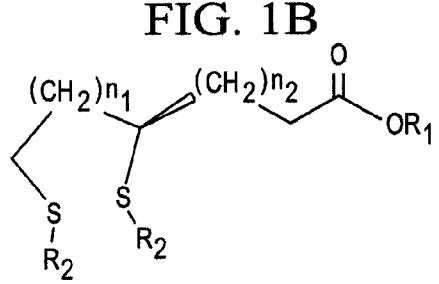
FIG. 1B is a chemical formula of other derivatives of alpha-lipoic acid or pharmaceutically acceptable salts or derivatives thereof.

The term "lipoic acid derivative" refers to molecules structurally related to alpha-lipoic acid, or a salt thereof such as sodium lipoate, that function as an antioxidant in vivo. A wide array of lipoic acid derivatives are known in the art and may be used according to the invention. For example, U.S. Pat. No. 6,887,891 (incorporated herein by reference in its entirety) details a number of lipoic acid derivatives any of which may be used in accordance with the invention. Certain generalized structures for lipoic acid derivative molecules are depicted in FIG. 1A-B. For example, a lipoic acid derivative may have a structure according to FIG. 1A wherein $n_1$ and $n_2$ are, independently, $C_1$-$C_{10}$ alkyl; and $R_1$ is H, $C_1$-$C_{10}$ alkyl, $C_6$-$C_{14}$ aryl, an alkyl ammonium or a protonated amino acid. Likewise, a lipoic acid derivative may have a structure according to FIG. 1B wherein $n_1$ and $n_2$ are, independently, $C_1$-$C_{10}$ alkyl; $R_1$ is H, $C_1$-$C_{10}$ alkyl, $C_6$-$C_{14}$ aryl, an alkyl ammonium or a protonated amino acid; and each of the $R_2$ positions are, independently, H, $C_1$-$C_{10}$ alkyl or $C_6$-$C_{14}$ aryl. Salts of alpha-lipoic acid with inorganic cations such as sodium, alkyl ammonium cations, and other pharmaceutically acceptable cations may be used according to the invention. Additionally, a number of esters and thioesters of alpha-lipoic acid can function as pro-drugs, undergoing hydrolysis to alpha-lipoic acid and dihydrolipoic acid in vivo.

In certain aspects, topical application of antioxidants (e.g., a lipoic acid derivative) to a wound is used to reduce ROS levels and to facilitate the normal healing process of a chronic wound. Other antioxidants for application in wound healing include ascorbic acid, fatty (linolenic, linoleic, and oleic) acids, and N-acetyl cysteine and such antioxidants may additionally be used in compositions disclosed herein. As demonstrated herein, alpha-lipoic acid and its derivatives are potent antioxidants. Major biological effects of alpha-lipoic acid, for example, include normalizing blood sugar levels, improving nerve blood flow, reducing oxidative stress, alleviating diabetic neuropathy, and protecting membranes. Other advantages of lipoic acid molecules over other antioxidants include high antioxidant activity, the ability to scavenge free radicals in both water and fatty tissues, stability to gamma sterilization, and prolonged shelf-life, which is particularly important for medical device applications. Limited solubility in water and moderate hydrophobicity of alpha-lipoic acid are preferable for formulations that require graduate sustained release of antioxidants. These properties combined with low cost of derivatives such as alpha-lipoic acid make it a preferable solution for treatment of chronic wounds in general, and for formulation into topical applications or application to a carrier material, such as wound dressing.

Although alpha-lipoic acid is stable to gamma-sterilization and temperatures up to 60° C., it may undergo partial decomposition in some storage conditions, like high humidity and low temperature, which is accompanied by an unpleasant odor due to its sulfur content. However, conversion of alpha-lipoic acid into a salt derivative, such as sodium lipoate, or the use of polymer barriers in the topical composition mitigates the odor issues. For example, a lipoic acid derivative may be converted to a salt at a pH of about 6 to about 8. Within this pH range lipoic acid derivatives, such as alpha-lipoic acid, can be efficiently converted to a salt to reduce odor without significant loss of antioxidant activity. Thus, in certain aspects, the invention provides compositions having reduced odor properties comprising a pharmaceutically acceptable salt of a lipoic acid derivative (e.g., sodium lipoate).

When the alpha-lipoic acid is converted enzymatically into dihydrolipoic acid, the dihydrolipoic acid is more potent than alpha-lipoic acid at neutralizing superoxide radicals, hydroperoxy radicals, hydroxyl radicals, and other major ROS and the antioxidant activity of the lipoic acid actually increases in the cells. Application of stable molecule of alpha-lipoic acid, which converts in the body into extremely potent antioxidant is highly advantageous from the handling and shelf-life perspectives. Thus, in certain aspects, a lipoic acid derivative for use according to the invention may be a lipoic acid prodrug that is converted into an active antioxidant in vivo.

Excessive MMP activity at a tissue site can also be addressed by providing a biologically active composition comprising a sacrificial proteolytic enzyme substrate, such as protein, protein hydrolysate, or combinations thereof. For example, a sacrificial proteolytic enzyme substrate can comprise keratin, collagen, elastin, gelatin, casein, albumin, fibrinogen, fibronectin, soy protein, wheat protein, corn protein, milk proteins and/or hydrolysates thereof (see, e.g., U.S. Pat. No. 6,500,443, incorporated herein by reference). In certain embodiments, proteins for use as sacrificial substrates are hydrolyzed or partially hydrolyzed by treatment with a strong acid or base. Such treatment can fragment the subject proteins and generate more accessible peptide sequence to bind to proteolytic enzymes.

The most prevalent MMPs in chronic wounds are the gellatinase proteases, MMP-2 and MMP-9 that more readily target the hydrolyzed or denatured form of collagen known as "gelatin." Thus, in certain aspects, a biologically active composition for use as described here further comprises a collagen, such as a hydrolyzed collagen (e.g., gelatin). Gelatin can be processed from a variety of sources including, but not limited to, bovine skin, pig skin and bone material. Depending on the hydrolysis methods employed in manufacture, the gelatin may be defined as a type A or type B gelatin. One advantage of using a gelatin rather than, or in addition to, collagen is that gelatin includes exposed peptide sequences that serve as signals for protease binding. Accessibility of signaling sequences in the native collagen molecule is diminished due to triple-helix structure of native collagen molecule, where polypeptide chains are bound with strong hydrogen bonds. Thus, in certain aspects, a biologically active composition is defined as not comprising collagen. In the case of gelatin, on the other hand, signaling sequences are readily exposed to proteases making it more efficient as a sacrificial substrate.

A primary constraint against using gelatin in wound dressings has been insufficient mechanical integrity and inability to maintain dressing shape in wound environment as is possible with natural collagen. However, if gelatin is applied as a coating onto another porous material, such as a bandage, gauze, or polyurethane foam, which will provide structural support, such material with gelatin may be an excellent choice as an MMP sacrificial substrate. Therefore, in one embodiment, gelatin for use in biologically active compositions can comprise a bloom value of between about 150-300 g, between about 200-250 g or about 225 g. In certain embodiments it may be beneficial to use gelatin with sufficient gel strength to form an adherent layer on a porous material without causing the material to become overly stiff.

Additionally, gelatin is an excellent oxygen barrier, which is important for stability of molecules that could be incorporated in wound dressings for instance, such as antioxidants and oxygen sensitive proteins and peptides. Thus, the carrier material within a wound dressing may be a polyurethane foam as described herein that is coated with gelatin to provide the reduced pressure dressing with a sacrificial substrate for MMPs. Biologically active compositions may, for example, comprise 0.1% to 25%, 1% to 10% or about 6%, 8%, 10%, 15% or 20% w/w gelatin.

In certain aspects, a biologically active composition, such as a composition applied to a carrier material is sterilized by irradiation. A skilled worker will recognize that such irradiation can alter the amount of cross-linking within proteins in the composition. Thus, in cases where the composition comprises a sacrificial proteolytic enzyme substrate that is a protein, such as gelatin, the amount of irradiation may be adjusted not only to achieve sterilization but also to achieve a desired level of protein cross-linking. For example, a gelatin with a relatively low bloom value can be used in a coating and then subjected to irradiation to increase the effective bloom value of the gelatin coating by further cross-linking the protein. In certain aspects, biologically active compositions and/or carrier material according to the invention are subjected to gamma irradiation, such as between about 10-80 Gy, about 20-60 Gy or about 30-50 Gy of radiation.

The compositions disclosed herein may further comprise other biologically active molecules such as antimicrobial agents, growth factors, proteinase inhibitors, chelating agent or preservatives. For example, in certain aspects the composition additionally comprises a metal chelating agent capable of reducing MMP activity, such as EDTA. Antimicrobial agents may also be used in compositions according to the invention. For example, the composition may include antibiotics, antifungal agents or more general antimicrobials. Antimicrobial compounds compatible with lipoic acid formulation include, but are not limited to, non-ionic silver, polyhexamethylene biguanide, chlorhexidine, benzalconium chloride, triclosan and others.

As described herein, the combination of a lipoic acid derivative and gelatin promotes healing or prophylaxis of chronic ulcers by regulating level of ROS and matrix metalloproteinases (MMP's) at the ulcer site. The balance between reactive oxygen species, proteolytic enzymes and their inhibitors is critical to the persistence and healing of chronic ulcers, and that the alpha-lipoic acid corrects this balance in chronic ulcers. Alpha-lipoic acid, for example, inhibits the influx of inflammatory cells to a wound site by inhibiting the transcription of genes for adhesion molecules such as ICAM-1 and other adhesion molecules on inflammatory cells and endothelial cells. The alpha-lipoic acid inhibits the activation of nuclear transcription factors such as NF-κB, which controls the transcription of the MMP-9 gene, adhesion molecule genes such as ICAM-1, and inflammatory mediator genes such as TNF-alpha. Finally, alpha-lipoic acid can interfere with the inflammatory mediators such as leukotrienes.

In one embodiment a topical composition of the present invention may be formulated into a wide variety of articles to be topically applied that include but are not limited to lotions, creams, gels, sticks, sprays, ointments, pastes, foams, powders and film-forming products. Such compositions may be formulated for time-controlled release of the lipoic acid derivative. For example, the formulation may be formulated such that the lipoic acid derivative is released over a period of about 12 hours, 24 hours, 2 days, 3 days 4 days or 1 or more weeks.

Such formulations may additionally contain pharmaceutically acceptable carriers, such as sugars, starches, cellulose, excipients, oils, glycols, polyols, esters, agar, and buffering agents. The above are non-limiting examples of carriers. Pharmaceutically acceptable carriers may be distinct from carrier materials described below and are known in the art. Pharmaceutically acceptable carriers other than those listed herein may be easily formulated by those of ordinary skill in the art.

A topical composition of the present invention may additionally comprise conventional adjuvants such as propionic acid, propylene glycol, acetone and lactic acid, conventional buffers, preservatives, hydrophilic emulsifiers, lipophilic emulsifiers, perfumes, emollients, deodorants, humectants and the like. Colorants may also optionally be added in the compositions of the present invention, adjuvants which would be harmful to the wound site or surrounding skin should be avoided, as well as those adjuvants which may react with and/or adversely reduce the effectiveness of the composition.

In another embodiment, application of a topical composition of the present invention may be infusion within, injection into, absorption by, layering on, encapsulation within or coating on, a carrier material, such as a bandage, gauze, wound dressings, adhesive bandages, scaffold, and hydrogels. A "carrier material" as used herein refers to a material suitable for having a lipoic acid derivative, a proteolytic enzyme or a combination thereof applied thereon. For example, a composition of alpha-lipoic acid and a proteolytic enzyme substrate may be applied to a woven, non-woven, or knitted fabric material, such as gauze, dispersed within film, sponge, or foam for sustained release at the wound. The carrier material may be either bioresorbable, for instance comprising polyglycolic acid, polylactic acid, polydioxanone, polyhydroxybutyrate, polyhydrozyvalerate, polyaminoacids polyorthoesters, polyvinly alcohol, collagen, gelatin, chitosan, oxidized regenerated cellulose, hyaluronic acid, alginate or derivatives thereof, or may be non-bioresorbable, comprising for instance, polyurethane, polyvinyl alcohol, or gauze. In particular embodiments, the carrier material may be made of the same substance as the proteolytic enzyme substrate, for instance collagen or a modified collagen, such as gelatin. In certain aspects, the composition may be bound to the carrier material, such as through hydrogen binding, covalent binding or ionic binding. Carrier materials are distinct from the pharmaceutically acceptable carriers defined above.

In one embodiment the lipoic acid derivative and proteolytic enzyme substrate are mixed, resulting in a homogenous mixture, prior to application to the carrier material. In an alternative embodiment, such application may be layered such that the lipoic acid derivative is deposited onto the carrier material first and the proteolytic enzyme substrate is deposited thereon or vice versa.

Compositions containing alpha-lipoic acid or the pharmaceutically acceptable salt or derivative thereof may be suitable for local or systemic, oral or parenteral administration. The examples of the administration of alpha-lipoic acid include a formulation comprising of 0.001% to 10% w/v, 0.1% to 10%, or 1% to 5% w/v lipoic acid derivative or salt thereof, within or coated onto an acceptable carrier material. Suitable carrier materials include, but are not limited to: bandages, gauze, wound dressings, adhesive bandages, scaffold, hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (Carbopols) as well as gelatin. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilizers such as EDTA. Biologically active compositions may, in some embodiments, contain one or more additional active agents.

In certain aspects, a biologically active composition is applied to the surface and into the pores of a carrier material. Methods for application to such a carrier material may, for example, comprise the steps of (i) saturating a porous substrate material with a solution comprising the components of a biologically active composition; and (ii) drying the porous substrate thereby producing a wound healing carrier material coated with a biologically active composition. For example, the coating solution may comprise a lipoic acid derivative (e.g., alpha-lipoic acid or sodium lipoate) and gelatin. In certain aspects, the substrate material is dried such that the resulting wound healing carrier material comprises a moisture content of less than about 5%. In an additional embodiment, the lipoic acid derivative and proteolytic enzyme substrate may be applied to the carrier material separately. For instance, the lipoic acid derivate may initially be applied to the carrier material, followed by application of proteolytic enzyme substrate, or vice versa.

The present invention may be useful for the treatment of wounds by any method where the topical composition is contacted with the wound site. For instance, through direct topical application of a cream, a gel, an ointment or a spray. In another embodiment contact with the wound site may be though the use of the topical composition of the present invention applied to a carrier material, which is then applied to the wound site. Such methods may include application of the composition to a bandage, gauze or wound dressing to be applied to the wound.

The formulation of lipoic acid and gelatin applied to a carrier material provides unique combination of effects and is highly effective for healing of chronic wounds. The formulation may be used in combination with negative pressure wound therapy, which is known to be highly effective in stimulating growth of granulation tissue, reducing infection and maintaining proper moisture balance in the wound. Addition of gelatin and lipoic acid to the dressing specifically addresses healing of chronic wounds removing barriers to normal healing such as abnormally high levels of ROS and MMPs. It should be noted that MMP aspect of wound healing is addressed by formulations described herein from several perspectives, i.e., the reduction of ROS levels to affect recruitment of MMPs and gelatin to service as sacrificial substrate for MMPs preserving newly formed granulation tissue. In another embodiment, EDTA may be added to the composition. The addition of EDTA may help to prevent MMP from activation.

According to one illustrative embodiment, a system is provided for treating a wound at a tissue site of a patient that includes a reduced-pressure source to supply reduced pressure and a manifold to distribute the reduced pressure to the wound. The system also includes a drape to cover the manifold and the wound to form a substantially sealed space over both. The manifold may be adapted for placement adjacent the wound and may function as a scaffold to support tissue growth. The system may also include a separate scaffold adapted for placement adjacent the wound to support tissue growth, and may also function as a manifold. In one embodiment, the manifold is coated with a biologically active composition including a lipoic acid derivative or any of its pharmaceutically acceptable salts and derivatives for treatment or prophylaxis of chronic wounds. The manifold may also comprise a collagen coating such a coating comprising gelatin. According to another illustrative embodiment, the scaffold is coated with a biologically active composition including a lipoic acid derivative or any of its pharmaceutically acceptable salts and derivatives, and may also comprise a collagen coating such as a coating comprising gelatin.

Figure 5:
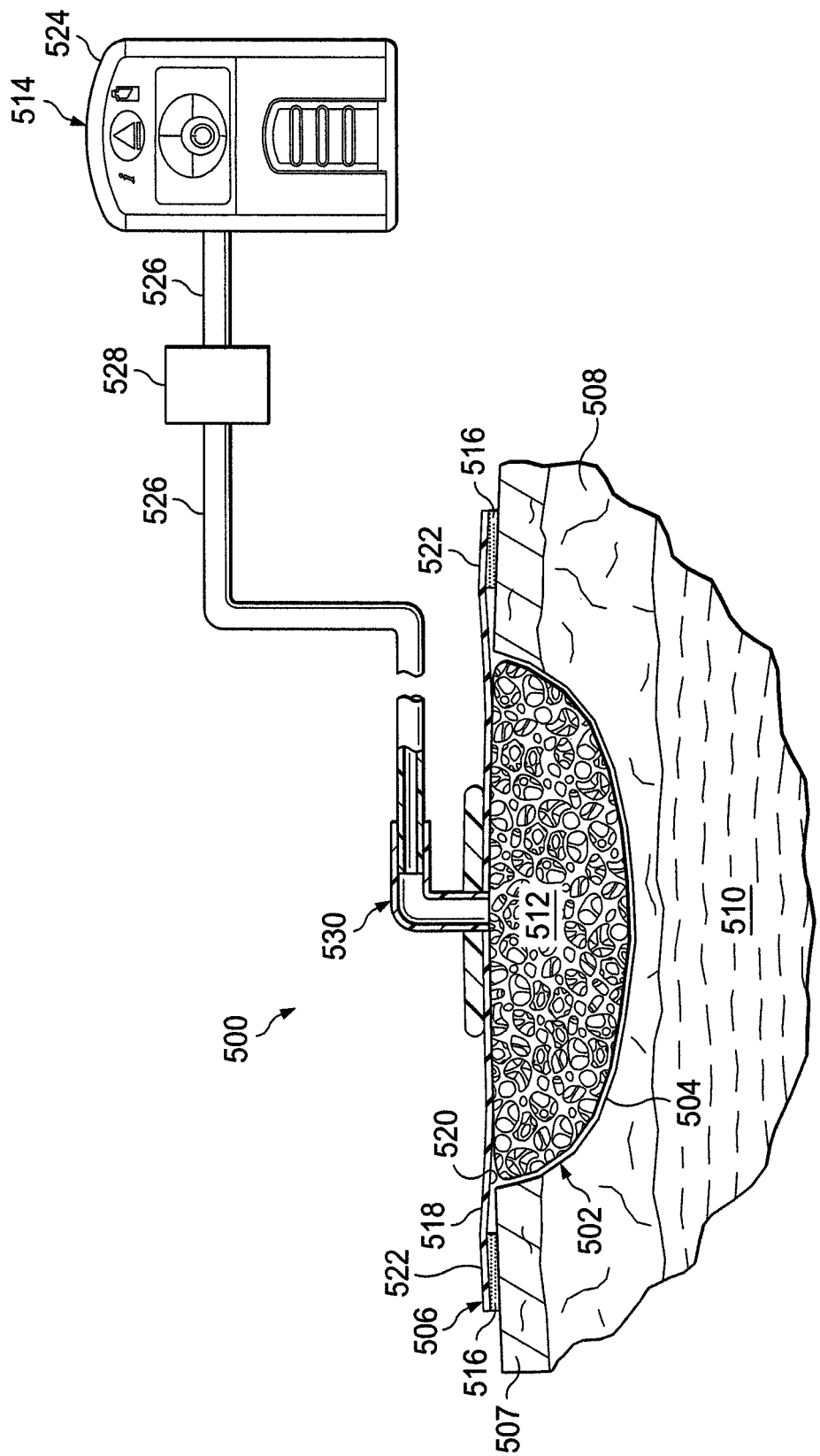
FIG. 5 is a schematic diagram with a portion shown in cross section of an illustrative embodiment of a reduced-pressure treatment system including wound dressing that utilizes a manifold.

Referring to FIG. 5, a reduced-pressure treatment system 500 for treating a tissue site 502 is presented that includes a drape 506. The tissue site 502 may be, for example, a wound 504. The wound 504 may include, without limitation, any irregularity with a tissue, such as an open wound, surgical incision, or diseased tissue. The wound 504 is shown extending through the epidermis 507, or generally skin, and the dermis 508 and reaching into a hypodermis, or subcutaneous tissue 510. The reduced-pressure treatment system 500 may be used to treat a tissue, such as a wound of any depth, as well as many different types of tissue sites including open wounds or intact tissue. The tissue site 502 may be the bodily tissue of any human, animal, or other organism, including bone tissue, adipose tissue, muscle tissue, dermal tissue, vascular tissue, connective tissue, cartilage, tendons, ligaments, or any other tissue.

The reduced-pressure treatment system 500 may include a manifold 512, the drape 506, and a reduced-pressure subsystem 514. The manifold 512 is operable to distribute reduced pressure. The drape 506 provides a fluid seal over the tissue site 502. "Fluid seal," or "seal," means a seal adequate to maintain reduced pressure at a desired site given the particular reduced-pressure source or subsystem involved. The drape 506 may be sized by the healthcare provider at the time of application by hand without requiring cutting tools. The reduced-pressure treatment system 500 may include an attachment device 516 to help form a fluid seal between the drape 506 and the patient's epidermis 507. The drape 506 has a first side 518 and a second, patient-facing side 520. The manifold 512 is positioned between the second, patient-facing (inward-facing) side 520 of the drape 506 and the tissue site 502.

The drape 506 may be sized to overlap the wound 504 in such a manner that a portion of the drape 506 extends beyond the periphery of the wound 504 to form an extension 522. The drape 506 may be formed from any material that provides a fluid seal. The drape 506 may, for example, be an impermeable or semi-permeable, elastomeric material. "Elastomeric" means having the properties of an elastomer. Elastomeric material generally refers to a polymeric material that has rubber-like properties. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones.

The attachment device 516 may be used to attach the adjustable covering 506 to the patient's epidermis 507 or another layer, such as a gasket or additional sealing member. The attachment device 516 may take numerous forms. For example, the attachment device 516 may be a medically-acceptable, pressure, sensitive adhesive that is applied to the extension 522 of the drape 506. Alternatively, the pressure-sensitive adhesive may span the entire width of the drape 506. Alternative attachment devices may include, but are not limited to, heat-activated adhesives, sealing tapes, double-sided sealing tapes, pastes, hydrocolloids, hydrogels, hooks, sutures, or other device.

The reduced-pressure subsystem 514 includes a reduced-pressure source 524 that provides reduced pressure through the drape 506 to the manifold 512. The reduced-pressure source 524 may be any device for supplying a reduced pressure, such as a vacuum pump, wall suction, or other source. While the amount and nature of reduced pressure applied to the tissue site 502 will typically vary according to the application, the reduced pressure will typically be between −5 mm Hg and −500 mm Hg and more typically between −100 mm Hg and −300 mm Hg. For example, and not by way of limitation, the pressure may be −90, −100, −110, −120, −130, −140, −150, −160, −170, −180, −190, −200 mm Hg or another pressure. The reduced pressure developed by the reduced-pressure source 524 is delivered through the reduced-pressure conduit 526, through canister 528, to a reduced-pressure interface 530. In one illustrative embodiment, the reduced-pressure interface 530 is a TRAC® technology port available from Kinetic Concepts, Inc. of San Antonio, Tex. The reduced-pressure interface 530 allows the reduced pressure to be realized within a sealed space below the drape 506 for distribution by the manifold 512.

The manifold 512 may be placed proximate the tissue site 502, e.g., wound 504. The drape 506 may be adjusted to the desired size and placed over the manifold 512 such that the extension 522 extends beyond the periphery of the wound 504. The extension 522 may be secured to the patient's epidermis 507 by the attachment device 516 in order to form a fluid seal over a portion of the patient's epidermis 507 and the manifold 512. The reduced-pressure interface 530 may then be applied, if not already installed. The reduced-pressure conduit 526 is fluidly coupled to the reduced-pressure interface 530 and fluidly coupled to the reduced-pressure source 524.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. The reduced pressure delivered may be constant, varied (patterned or random) and may be delivered continuously or intermittently. Unless otherwise indicated, values of pressure stated herein are gauge pressures. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

The term "manifold" as used herein generally refers to a substance or structure that is provided to assist in applying reduced pressure to, delivering fluids to, or removing fluids from a tissue site, e.g., tissue site 502. The manifold 512 typically includes a plurality of flow channels or pathways to distribute fluids provided to and remove fluids from around the manifold 512. The plurality of flow channels or pathways may be interconnected. The manifold 512 may be a biocompatible material that is capable of being placed in contact with a tissue site, e.g., tissue site 502, and distributing reduced pressure to the tissue site 502. Examples of manifold members may include, without limitation, devices that have structural elements arranged to form flow channels, such as, for example, cellular foam, open-cell foam, porous tissue collections, and foams that include, or cure to include, flow channels. Thus, for example, the manifold 512 may be porous and may be made from foam, gauze, felted mat, or other material. The manifold 512 may be formed directly from a porous material, e.g., a foam, or from a material that is made porous, e.g., a solid member in which apertures have been applied. The foam material may be either hydrophobic or hydrophilic.

As a non-limiting example, the porous foam may be a polyurethane, open-cell, reticulated foam, such as a GranuFoam® material manufactured by Kinetic Concepts, Incorporated of San Antonio, Tex., or Granufoam Silveri® material manufactured by Kinetic Concepts, Incorporated of San Antonio, Tex. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity. In one embodiment, the distribution manifold 130 may be constructed from bioresorbable materials that do not have to be removed from a patient's body following use of the wound dressing. Suitable bioresorbable materials may include, without limitation, collagen or a polymeric blend of polylactic acid (PLA) and polyglycolic acid (PGA). The polymeric blend may also include, without limitation, polycarbonates, polyfumarates, and capralactones. Other bioresorbable materials that may be used include, but are not limited to, polydioxanone, polyhydroxybutyrate, polyhydrozyvalerate, polyaminoacids polyorthoesters, polyvinly alcohol, chitosan, oxidized regenerated cellulose, hyaluronic acid, alginate, collagen, a modified collagen, such as gelatin or derivatives of any of the above.

The manifold 512 or portion thereof may further serve as a scaffold for new cell-growth, or a separate scaffold (not shown) may be used in conjunction with the manifold 512 to promote cell-growth as described above. Thus, a scaffold may also function as a manifold in accordance with the embodiments described herein to administer reduced pressure tissue treatment to a tissue site. Although one skilled in the art recognizes that the manifold 512 may also function as a scaffold, the illustrative embodiments herein do not specifically show the use of a separate scaffold structure in conjunction with the manifold 512. The scaffold and/or manifold, together or separately referred to sometimes as wound dressing, may be also be infused with, coated with, or comprised of cells, growth factors, extracellular matrix components, nutrients, integrins, or other substances to promote cell growth. The wound dressing may also function as a carrier material further comprising a biologically active composition such as those described herein including, for example, a composition comprising a lipoic acid derivation or gelatin. In another embodiment, system 500 may comprise a separate carrier material in addition to the wound dressing components.

Scaffolds may be formed from biologic or synthetic scaffold materials, and are used in the field of tissue engineering to support protein adhesion and cellular ingrowth for tissue repair and regeneration. The current state of the art in scaffold technology relies upon the inherent characteristics of the surrounding tissue space for the adsorption of proteins and migration of cells. Nonlimiting examples of suitable scaffold materials include extracellular matrix proteins such as fibrin, collagen or fibronectin, and synthetic or naturally occurring polymers, including bioabsorbable or non-absorbable polymers, such as polylactic acid (PLA), polyglycolic acid (PGA), polylactide-co-glycolide (PLGA), polyvinylpyrrolidone, polycaprolactone, polycarbonates, polyfumarates, caprolactones, polyamides, polysaccharides (including alginates (e.g., calcium alginate) and chitosan), hyaluronic acid, polyhydroxybutyrate, polyhydroxyvalerate, polydioxanone, polyorthoesthers, polyethylene glycols, poloxamers, polyphosphazenes, polyanhydrides, polyamino acids, polyacetals, polycyanoacrylates, polyurethanes (e.g., GranuFoam®), polyacrylates, ethylene-vinyl acetate polymers and other acyl substituted cellulose acetates and derivatives thereof, polystyrenes, polyvinyl chloride, polyvinyl fluoride, poly(vinylimidazole), chlorosulphonated polyolefins, polyethylene oxide, polyvinyl alcohol, Teflon®, and nylon.

The scaffold can also comprise ceramics such as hydroxyapatite, coralline apatite, calcium phosphate, calcium sulfate, calcium carbonate or other carbonates, bioglass, allografts, autografts, xenografts, decellularized tissues, or composites of any of the above. In particular embodiments, the scaffold comprises collagen (e.g., Biostep™ or Pomogran™ scaffolds), polylactic acid (PLA), polyglycolic acid (PGA), polylactide-co-glycolide (PLEA), a polyurethane, a polysaccharide, an hydroxyapatite, or a polytherylene glycol. Additionally, the scaffold can comprise combinations of any two, three or more materials, either in separate or multiple areas of the scaffold, combined noncovalently or covalently (e.g., copolymers such as a polyethylene oxide-polypropylene glycol block copolymers, or terpolymers), or combinations thereof.

Figure 6A:
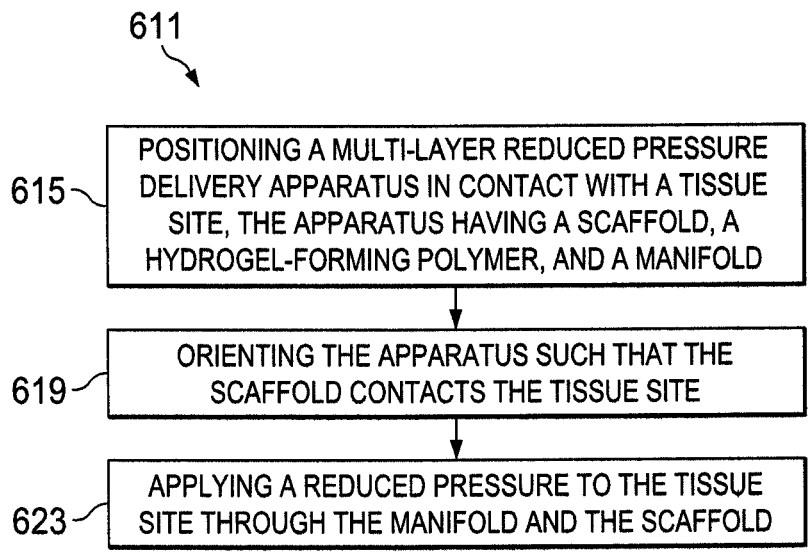
FIG. 6A illustrates a method of promoting new tissue growth at a tissue site according to one embodiment.

Referring to FIG. 6A, a method 611 of promoting tissue growth at a tissue site according to an embodiment of the present invention is illustrated. The method 611 includes positioning a multi-layer reduced pressure delivery apparatus in contact with the tissue site at 615. The reduced pressure delivery apparatus includes a scaffold, a release material, and a manifold. At 619, the apparatus is oriented such that the scaffold contacts the tissue site. A reduced pressure is applied to the tissue site through the manifold and the scaffold at 623.

Figure 6B:
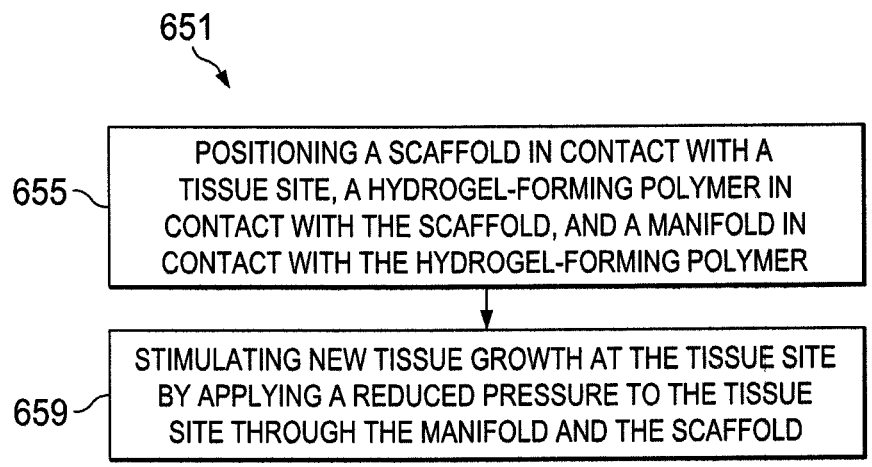
FIG. 6B depicts a method of promoting new tissue growth at a tissue site according to another embodiment.

Referring to FIG. 6B, a method 651 of promoting new tissue growth at a tissue site according to an embodiment of the present invention is illustrated. The method 651 includes at 655 positioning a scaffold in contact with the tissue site, a release material in contact with the scaffold, and a manifold in contact with the release material. At 659, new tissue growth is stimulated at the tissue site by applying a reduced pressure to the tissue site through the manifold and the scaffold.

EXAMPLES

The following examples are included to demonstrate certain embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Polyurethane open-cell reticulated foam pads were selected as the scaffold and were immersed in a solution containing 1.5 wt % of alpha-lipoic acid and 4.5 wt % 225-bloom beef gelatin (and, where applicable, 0.3% EDTA). Gelatin was used as a biocompatible binding agent with good oxygen barrier and sustained release properties for alpha-lipoic acid as well as for its ability to act as a sacrificial substrate for surrounding gelatinases. Alpha-lipoic acid was pre-dissolved in ethanol and then mixed into the final solution. The foam pads were immersed for a sufficient amount of time to coat the pathways formed within the open-cell reticulated foam as described above with respect to the scaffold. After immersion, the foam pads were withdrawn, compressed to remove excess solution, and dried to a constant weight. In some cases, sodium benzoate was added to the formulation as a preservative. Dried foams comprised, by weight, 2% alpha-lipoic acid, 6% gelatin and, where applicable, 0.4% EDTA.

Figure 2:
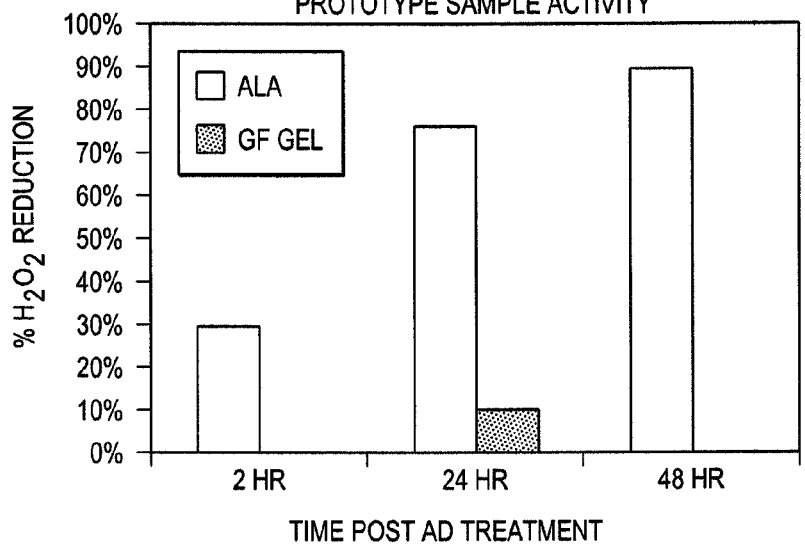
FIG. 2 is a graph showing antioxidant activity for scaffolds containing alpha-lipoic acid.
Figure 3:
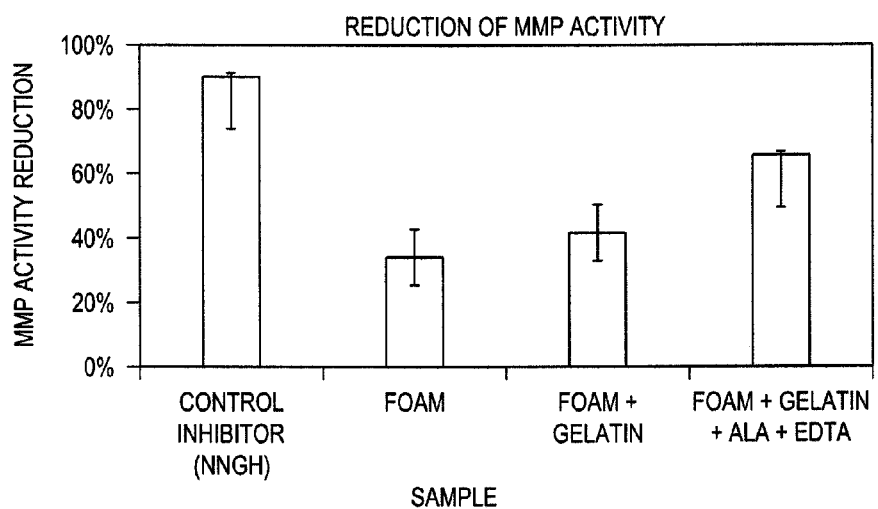
FIG. 3 is a chart showing the reduction of MMP activity for scaffolds containing alpha-lipoic acid and gelatin as compared to controls.
Figure 4:
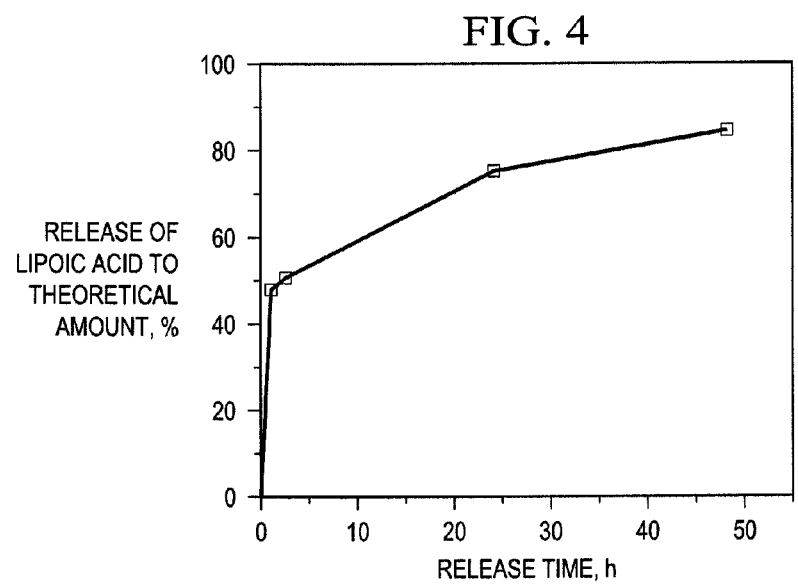
FIG. 4 is a chart showing the release profile of alpha-lipoic acid from coating on a scaffold.

A National Diagnostics Hydrogen Peroxide Assay Kit was used to evaluate the antioxidant properties of foam pads and the formulated coated foam pads containing alpha-lipoic acid. Foam pads coated only with gelatin were used as controls. FIG. 2 is a graph showing the percentage of hydrogen peroxide reduction due to reaction with alpha-lipoic acid. An MMP-9 Colorimetric Drug Discovery Kit (Biomol) was used to evaluate the MMP inhibiting/inactivating ability of the formulated foam pads containing alpha-lipoic acid/gelatin (ALA) and gelatin alone (GF GEL). The controls were uncoated foam pads and known potent MMP inactivating drug, NNGH ($C_{13}H_{20}N_2O_5S$, available from Enzo® Life Sciences). FIG. 3 is a graph showing that gelatin-coated foam pads inhibit MMP activity, but the combination of gelatin and ALA along with the EDTA (described in Example 2) are much more potent than gelatin alone. FIG. 4 is a graph showing the release of alpha-lipoic acid from the coating on the foam pads. The coating delivers approximately 70% of the total alpha-lipoic acid within the first day, while the remaining alpha-lipoic acid is released during the next 2-3 days.

Example 2

Chelating agents like ethlenediaminetetraacetic acid (EDTA) were added to the dipping solution described in Example 1. The addition of EDTA to wound dressings prevents MMP from activation chelating zinc ions essential for activation of pro-MMPs.

Example 3

A solution of sodium hydroxide can be added to the dipping solution described in Examples 1-2 to convert lipoic acid into sodium lipoate. The pH of resulting solution should be in the range between 6 and 8. The conversion of lipoic acid into sodium lipoate eliminates the risk of development of sulphur odor in the coated foams.

Example 4

Coated polyurethane foam (GranuFoam®) scaffolds described above in Examples 1-2 were further assayed for their ability to reduce MMP activity as compared to non-coated collagen based scaffold such as the Biostep™ and Promogran™ products. The results from two separate experiments are presented below in Tables 1 and 2 and demonstrate that the coated scaffolds reduced MMP activity similarly to collagen scaffolds, even though the coated scaffolds only comprised 10% by weight biologically active layer.

TABLE 1

| Dressing treatment | % MMP-9 activity reduction* | Standard deviation |
| --- | --- | --- |
| NNGH | 90.2 | 1.2 |
| Foam | 34.5 | 9.6 |
| Foam + gelatin | 42.2 | 8.4 |
| Foam + gelatin + ALA + EDTA | 65.8 | 0.0 |
| Promogran ™ | 68.7 | 0.5 |
| Biostep ™ | 82.2 | 1.8 |

*All values indicate the amount of MMP-9 activity reduction as compared to control samples with no MMP-9 inhibitor activity.
ALA indicates alpha-lipoic acid coating.

TABLE 2

| Dressing treatment | % MMP-9 activity reduction* | Standard deviation |
| --- | --- | --- |
| NNGH | 103.8% | 2.1 |
| Foam | 27.1% | 0.2 |
| Foam + gelatin | 72.6% | 21.8 |
| Foam + gelatin + EDTA | 54.5% | 3.5 |
| Foam + gelatin + ALA + EDTA | 90.4% | 1.9 |
| Promogran ™ | 100.8% | 4.5 |
| Biostep ™ | 104.6% | 3.0 |

*All values indicate the amount of MMP-9 activity reduction as compared to control samples with no MMP-9 inhibitor activity.
ALA indicates alpha-lipoic acid coating.

Example 5

The radiation stability of alpha-lipoic acid coated scaffolds described above were assessed by measuring the effectiveness of scaffold at decreasing ROS after gamma irradiation. Briefly, irradiated and control scaffolds were treated with 20 µM $H_2O_2$. Peroxide concentration was then measured using a TBR4100 with HPO-100 sensor (available from World Precision Instruments) at 2 hours or 24 hours after treatment. The results of these studies are summarized in Table 3. Results represent the average peroxide reduction measured in 10 replicates. As shown, the alpha-lipoic acid coating remained highly active (i.e., as an antioxidant) even after extensive irradiation.

TABLE 3

| Dressing irradiation treatment | ROS reduction 2 hr. | ROS reduction 24 Hours |
| --- | --- | --- |
| Foam alone control (0Gy) | 19% | 31% |
| 30 Gy | 45% | 83% |
| 40 Gy | 55% | 87% |
| 50 Gy | 59% | 86% |
| 60 Gy | 59% | 85% |

Example 6

A solution for administration to a wound site to promote healing is prepared by mixing an effective amount of a lipoic acid derivative, gelatin and an aqueous or organic solvent. The resulting solution contains from about 50% to about 99.99% aqueous or organic solvent. The solvent may be selected from, but is not limited to, propylene glycol, polyethylene glycol, polyproylene glycol, glycerol, 1,2,4-butanetriol, sorbiol esters, 1,2,6-hexanetriol, ethanol and mixtures thereof. Additional components or adjuvants are added as desired and appropriate.

Example 7

A lotion, cream or ointment for administration to a wound site to promote healing is prepared from the solution of Example 6 and further contains at least one emollient. The resulting lotion comprises about 1% to about 20% emollient and about 50% to about 90% water. The resulting cream comprises about 5% to about 50% emollient and from about 45% to about 85% water.

A simple base of animal, vegetable or synthetic oils or semi-solid hydrocarbons and a thickening agent are mixed into the ointment. The resulting ointment comprises from about 2% to about 10% emollient and about 0.1% to about 2% of a thickening agent.

Example 8

A therapeutic amount of the solution, lotion, cream or ointment from Examples 6 and 7 are applied to a wound site for a time effective to promote wound healing. The solution, lotion cream or ointment when applied and maintained for an appropriate amount of time results in reduced inflammation and increased tissue growth.

While the systems and methods of the present invention have been described with reference to tissue growth and healing in human patients, it should be recognized that these systems and methods for applying reduced pressure tissue treatment can be used in any living organism in which it is desired to promote tissue growth or healing. Similarly, the systems and methods of the present invention may be applied to any tissue, including without limitation bone tissue, adipose tissue, muscle tissue, dermal tissue, vascular tissue, connective tissue, cartilage, tendons, or ligaments. While the healing of tissue may be one focus of applying reduced pressure tissue treatment as described herein, the application of reduced pressure tissue treatment may also be used to generate tissue growth in tissues that are not diseased, defective, or damaged. For example, it may be desired to apply reduced pressure tissue treatment to grow additional tissue at a tissue site that can then be harvested. The harvested tissue may be transplanted to another tissue site to replace diseased or damaged tissue, or alternatively the harvested tissue may be transplanted to another patient.

Although the present invention and its advantages have been disclosed in the context of certain illustrative, non-limiting embodiments, it should be understood that various changes, substitutions, permutations, and alterations can be made without departing from the scope of the invention as defined by the appended claims.

We claim:

1. A system for treating a wound at a tissue site, comprising:
   a pressure source to supply reduced pressure;
   wound dressing in fluid communication with said pressure source to distribute reduced pressure to the wound, said wound dressing having a first portion contacting the wound and a second portion;
   a lipoic acid derivative and a sacrificial proteolytic enzyme applied to the second portion of said wound dressing; and
   a drape adapted to cover said wound dressing and the wound to provide a sealed space for applying the reduced pressure to the wound.

2. The system of claim 1, wherein the first portion of said wound dressing is a scaffold.

3. The system of claim 2, wherein the lipoic acid derivative and the sacrificial proteolytic enzyme are applied to the scaffold.

4. The system of claim 1, wherein the wound dressing further comprises a scaffold.

5. The system of claim 4, wherein the scaffold is comprised of polyurethane or collagen.

6. The system of claim 4, wherein the lipoic acid derivative and the sacrificial proteolytic enzyme are applied to the scaffold.

7. The system of claim 1, wherein the lipoic acid derivative and the sacrificial proteolytic enzyme are combine in a homogenous mixture.

8. The system of claim 7, wherein the homogenous mixture is applied to both the first portion and the second portion of said wound dressing.

9. The system of claim 7, wherein the homogenous mixture is applied to the surface of said wound dressing.

10. The system of claim 7, wherein the homogenous mixture is applied to internal portions of said wound dressing.

11. The system of claim 1, wherein the sacrificial proteolytic enzyme substrate comprises gelatin.

* * * * *

UNITED STATES PATENT AND TRADEMARK OFFICE
CERTIFICATE OF CORRECTION

PATENT NO. : 8,597,264 B2
APPLICATION NO. : 13/071387
DATED : December 3, 2013
INVENTOR(S) : Dmitry Zimnitsky, Jenny Finkbiner and Blane Sanders It is certified that error appears in the above-identified patent and that said Letters Patent is hereby corrected as shown below:

On the Title Page

Item (75) in the Inventors, add --Blane Sanders, San Antonio, TX (US)--

Signed and Sealed this
Third Day of June, 2014

Michelle K. Lee
*Deputy Director of the United States Patent and Trademark Office*